(12) United States Patent
Becker

(10) Patent No.: US 11,284,771 B2
(45) Date of Patent: Mar. 29, 2022

(54) WETTING DEVICE FOR FLAT MOPS

(71) Applicant: Hydroflex Group GmbH, Gladenbach (DE)

(72) Inventor: Edward Becker, Gladenbach (DE)

(73) Assignee: Hydroflex Group GmbH, Gladenbach (DE)

( * ) Notice: Subject to any disclaimer, the term of this patent is extended or adjusted under 35 U.S.C. 154(b) by 157 days.

(21) Appl. No.: 16/119,760

(22) Filed: Aug. 31, 2018

(65) Prior Publication Data

US 2020/0069144 A1 Mar. 5, 2020

(51) Int. Cl.
*A47L 13/50* (2006.01)
*A47L 13/256* (2006.01)
*A61L 2/04* (2006.01)

(52) U.S. Cl.
CPC ............. *A47L 13/50* (2013.01); *A47L 13/256* (2013.01); *A61L 2/04* (2013.01)

(58) Field of Classification Search
CPC ........ A47L 13/256; A47L 13/51; A47L 13/58; A47L 13/59; A61L 2/04
See application file for complete search history.

(56) References Cited

U.S. PATENT DOCUMENTS

| | | | |
|---|---|---|---|
| 3,775,802 A * | 12/1973 | Grassman | A47L 13/254 15/147.2 |
| 5,492,237 A * | 2/1996 | Chang | A47L 19/04 211/118 |
| 6,460,231 B2 * | 10/2002 | Bourgerie | A01K 97/08 24/487 |
| 6,889,917 B2 * | 5/2005 | Fahy | A47L 13/22 239/525 |
| 2002/0073502 A1 * | 6/2002 | Gromnicki | A47L 13/59 15/261 |
| 2005/0109378 A1 * | 5/2005 | Landsiedel | A47L 15/14 134/135 |
| 2005/0181968 A1 * | 8/2005 | Policicchio | A47L 11/4008 510/438 |
| 2016/0081527 A1 * | 3/2016 | Fodrocy | A47L 13/254 15/147.2 |

(Continued)

FOREIGN PATENT DOCUMENTS

| | | | | |
|---|---|---|---|---|
| EP | 2 106 730 A1 | 10/2009 | | |
| EP | 2 832 279 A1 | 2/2015 | | |
| EP | 2923626 A2 * | 9/2015 | ............. | A47L 13/50 |

*Primary Examiner* — Joseph L. Perrin
*Assistant Examiner* — Irina Graf
(74) *Attorney, Agent, or Firm* — Seed Intellectual Property Law Group LLP

(57) ABSTRACT

A wetting device for flat mops includes a mechanical elevator that contains a contact structure, brackets, and plastic slide bars. The brackets lift the transfer plate away from the lower end of the wetting device if the contact structure is pressed towards the lower end. Each bracket is connected to at least one plastic side bar. The plastic slide bars move apart from each other when the transfer plate lifts away from the lower end. The transfer plate lies upon the plastic slide bars during movement of the plastic slide bars apart from each other. Each plastic slide bar has a length that is at least five times larger than its maximum width and is detachable from its corresponding bracket. The contact structure is a flat metal framework of connected struts. Also disclosed is a cleaning trolley with the wetting device.

19 Claims, 9 Drawing Sheets

(56) References Cited

U.S. PATENT DOCUMENTS

| | | | |
|---|---|---|---|
| 2016/0128544 A1* | 5/2016 | Ben-Haim | A47L 15/505 211/41.9 |
| 2016/0249783 A1* | 9/2016 | Oh | A47L 19/04 211/41.4 |
| 2017/0303685 A1* | 10/2017 | Rehage | A47B 88/43 |

* cited by examiner

WETTING DEVICE FOR FLAT MOPS

BACKGROUND

Technical Field

This disclosure relates to a wetting device for moisturizing flat mops with a liquid, e.g., an aqueous cleansing liquid. It also relates to a cleaning trolley with said wetting device.

Description of the Related Art

Flat mops are known to have heads that are attachable to textile material covers for cleaning floors, e.g., rectangular microfiber covers. Said textile material covers usually comprise pockets for attachment to the mop head. Such mopping devices for cleaning of floors are widely known and used in professional and non-professional environments.

Wetting devices may be used to transfer a controlled amount of liquid upon a flat mop head with a textile material cover.

EP 2 106 730 A1 discloses a device for wetting a surface, consisting of a transfer member which can be arranged in a container filled with liquid, and means for moving the transfer member out of the container to the surface for wetting. The transfer member can be plate-like and have means for dosing liquid, while the moving means can be adapted to hold the transfer member horizontal during its movement. The moving means can comprise a pressing part which can be operated by the surface for wetting and which can be moved in opposite direction to the transfer member. The moving means can comprise for this purpose a number of arms which are mounted movably in a frame and which are connected on one side to the pressing part and on the other to the transfer member.

EP 2 832 279 B1 discloses a cleaning unit for cleaning clean rooms, comprising at least one first container, designed and arranged to accommodate at least one receiving element, designed and adapted to receive a liquid, and further comprising at least one second container, designed and set up, to receive a cleaning fluid, wherein the at least one second container comprises a transfer device, wherein the transfer device can be transferred from a first position to a second position, so that in the second position a certain amount of cleaning liquid on the transfer unit is available.

One of the problems associated with wetting devices known in prior art is that in clean rooms there still is some particle emission that should be avoided. Also the control of the exact amount of liquid needs to be improved when wetting flat mops.

Another problem associated with wetting devices is that they are no as easy to decontaminate as one might desire.

BRIEF SUMMARY

The wetting device for moisturizing flat mops with a liquid of the various embodiments may produce less particles, which makes said embodiments particularly suitable for use in clean rooms. The wetting device for moisturizing flat mops with a liquid of the various embodiments may enable a cleaner to transfer a precisely defined amount of liquid to a flat mop head, e.g., a flat mop head having a microfiber textile cover. The various embodiments may enable an efficient decontamination of the wetting device.

In accordance with some embodiments of the present disclosure the wetting device for flat mops comprises an upper end, a lower end, a transfer plate for liquid and a mechanical elevator, wherein the mechanical elevator contains a contact structure, brackets and plastic slide bars, wherein the brackets lift the transfer plate away from the lower end, if the contact structure is pressed towards the lower end and each bracket is connected to at least one plastic slide bar, wherein the plastic slide bars move apart from each other when the transfer plate lifts away from the lower end and wherein the transfer plate lies upon said plastic slide bars during said movement of the slide bars apart from each other.

According to a preferred example of the present disclosure the plastic slide bars are clip holders, each having two clamping thighs that clamp the corresponding bracket.

According to another preferred example of the present disclosure the plastic slide bars comprise or are made from polyacetals, polyethersulfones, polysulfones, polyether ketones, polyketones, polybutylene terephthalate or polytetrafluoroethylene. Rather suitable polymer materials include polyacetals such as polyoxymethylene.

According to some further embodiments the plastic slide bars have a length that is at least five times as large as the maximum width and/or each plastic side bar is detachable.

According to a further embodiment the plastic slide bars each have at least one rounded edge over which the transfer plate glides when the brackets lift the transfer plate away from the lower end.

In some embodiments two opposing central connection plates are pivotably connected to with their upper arms to two opposing lateral brackets and the opposing lower arms of the connection plates are mounted in opposing curved slits of an enclosure, wherein the brackets are also pivotably connected to said enclosure. The slits should be curved to compensate the movements of both brackets.

According to some further embodiments the contact structure is a flat metal framework of connected struts. In these embodiments the struts may have a thickness that equals at least 20% of the width of the struts. Also the struts may form adjacent triangular structures.

In some embodiments the wetting device comprises an enclosure with a first lateral side, a second lateral side and a bottom side, wherein the mechanical elevator is connected to the first and second lateral side. In some of these embodiments the mechanical elevator may be detachably connected to the first and second lateral side by fastening means. Also in some of these embodiments the first and second lateral sides each may comprise a rectangular frame with an internal plate that has two arms connected to the upper side of the rectangular frame and one arm connected to the lower side of the rectangular frame, wherein the lower side of the rectangular frame is connected to the bottom side of the enclosure. The enclosure may be a monobloc piece of metal.

According to a preferred example the transfer plate has a plate bottom and two opposing end sections with raised edges and at least one opening for liquid between said end sections. The two opposing end sections may be enclosed by raised edges in three directions. The at least one opening for liquid between said end sections may limit the raised edges and may be partially formed in the plate bottom and/or may have a length that is at least 25% of the total length of the plate.

In some embodiments the mechanical elevator comprises at least one removable plastic fluid displacer. Said removable plastic fluid displacer may comprise recesses for receiving the brackets.

Also the wetting device may be made from metal apart from the plastic slide bars and/or plastic fluid displacer.

Another example in accordance with the present disclosure is a wetting device, comprising an upper end, a lower end, a transfer plate for liquid and a mechanical elevator, wherein the mechanical elevator contains a contact structure and lifts the transfer plate away from the lower end, if the contact structure is pressed towards the lower end, wherein the transfer plate has two opposing end sections with raised edges and at least one opening for liquid between said end sections.

Another example in accordance with the present disclosure is a wetting device, comprising an upper end, a lower end, a transfer plate for liquid and a mechanical elevator, wherein the mechanical elevator contains a contact structure and lifts the transfer plate away from the lower end, if the contact structure is pressed towards the lower end, wherein the mechanical elevator comprises at least one removable plastic fluid displacer.

The present disclosure also relates to a cleaning trolley with one of the above described wetting devices.

DETAILED DESCRIPTION

Figure 1:
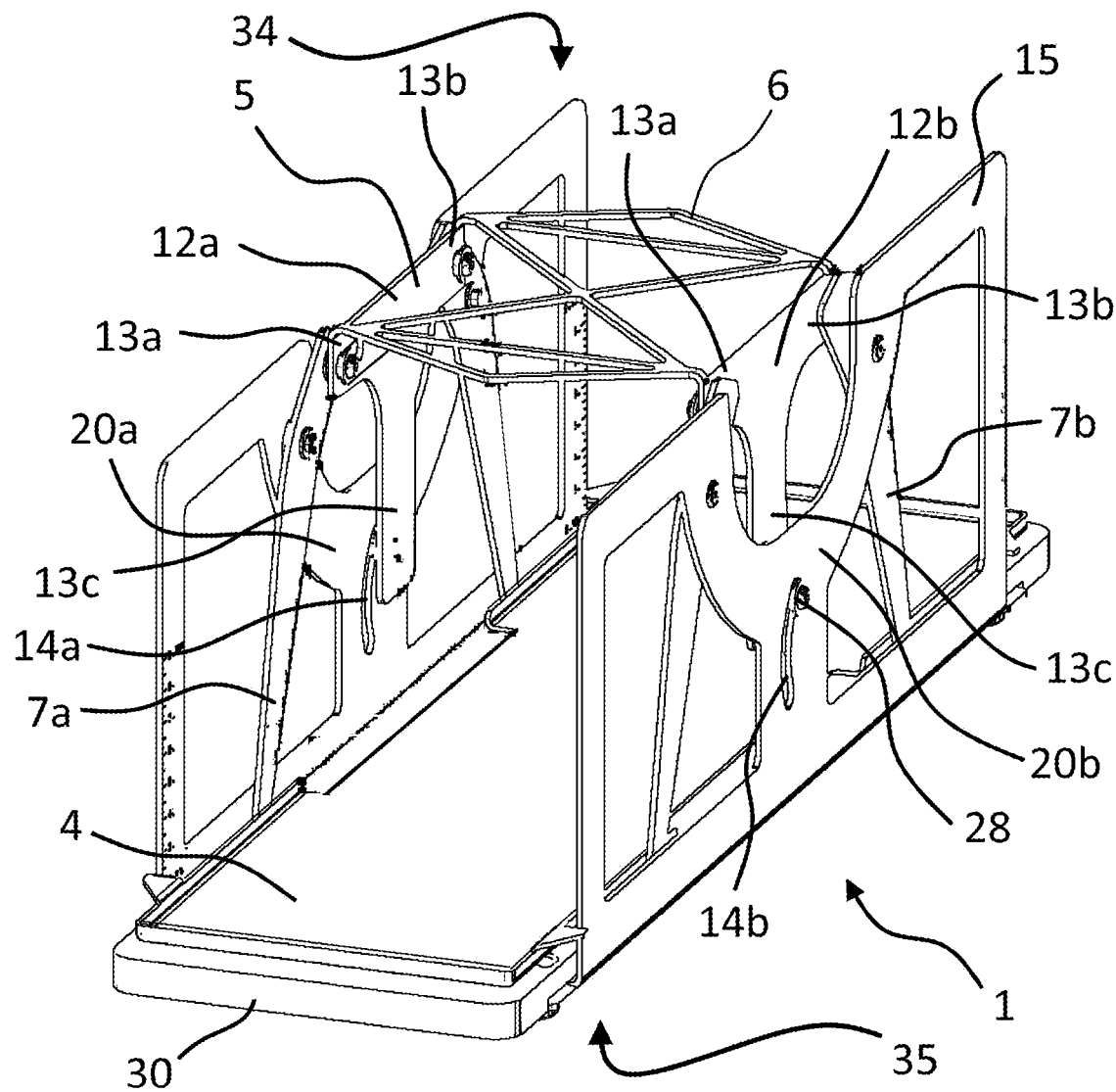
FIG. 1 shows a perspective view of an embodiment of wetting device with the transfer plate in a lowered position.

The present disclosure relates to a wetting device for flat mops with an upper end and an opposing lower end, comprising a transfer plate for liquid as well as a mechanical elevator, wherein the mechanical elevator contains a contact structure, brackets and plastic slide bars, wherein the brackets lift the transfer plate away from the lower end, if the contact structure is pressed towards the lower end and each bracket is connected to at least one plastic slide bar, wherein the plastic slide bars move apart from each other when the transfer plate lifts away from the lower end and wherein the transfer plate lies upon said plastic slide bars during said movement of the slide bars apart from each other. In some embodiments the wetting device comprises exactly two plastic slide bars.

The plastic slide bars release less particles than the brackets, which is important for clean rooms. In some embodiments the brackets comprise metal or are made out of metal. Before the application of plastic slide bars the release of particles by metal was thought to be lower than the release of particles by a plastic. However, it seems that the direct connection of metals may result in an increased particle release. With a plastic slide bar the transfer plate contacts a softer material and releases less particles, in particular if the transfer plate is made of metal. It was also found that the amount of liquid transferred may be more precise using plastic slide bars, which may be due to a decrease of tugs or jerks in view of improved gliding properties and/or less danger of interlocking.

A mechanical elevator is to be understood as a mechanical mechanism for lifting liquid. When the contact structure is pressed downwards, the force exerted upon the contact structure is transmitted as mechanical power and used to lift the transfer plate that contains liquid.

In some embodiments the mechanical elevator may be disposed within a container, in particular within an enclosure that is disposed within the container. It may also instead be sold without a container and be disposed in a suitable container when in use. Also it is in some embodiments possible that the wetting device comprises a container with a container bottom. Usually the container bottom would be at or next to the lower end of the wetting device. However, also without a container a wetting device may be provided that is suitable for use within container, wherein said container is not part of the wetting device. It is also not necessary (but possible) to attach the wetting device to the container.

When the transfer plate is close to the lower end during use it usually is at least partially submerged in liquid. A container may be partially filled with said liquid to a level that ensures that the transfer plate is submerged in der lower position at the bottom of the container. When the transfer plate is lifted as described above it will also lift beyond the liquid level of the container and retain a specific amount of liquid that is lifted together with the transfer plate. When a textile material cover contacts said liquid it will take up some or most of the liquid. It was found that a contact structure with openings allows a more uniform wetting of the textile material cover. The contact structure may be system of interconnected struts with such openings in between, in particular wherein the maximum width of said struts is multiple times thinner than the maximum diameter of said openings.

In some embodiments the plastic slide bars are detachably connected to the brackets. It was found to be advantageous if the plastic slide bars are detachable from the corresponding brackets. The wetting device may be made in some embodiments mainly from metal, wherein the metal parts are autoclavable. Thoroughness of decontamination with an autoclave may be improved if the plastic slide bars can be removed. The detachable plastic slide bar may be rigid.

In some embodiments the plastic slide bars may be detachable clip holders, each clip holder having two clamping thighs that clamp the corresponding bracket. The clip holders each may have a first clamping thigh and a second clamping thigh, which are connected at a clip elbow. Although various methods for detachably connecting the plastic slide bar to the bracket are possible in principle, e.g., using metal or plastic screws, it was found that clip holders result in less particle emission than screws or bolts. With clip s the force is spread more widely than with screws and it may be that this is at least partially the cause for less particle emission due to less intermittent stress.

In a preferred example the plastic slide bars are made from a thermoplastic material, e.g., polyoxymethylene. Thermoplastics such as polyacetals were found to be especially robust having excellent gliding properties. Among polyacetals polyoxymethylene was found to be particularly suitable. This material helps to decrease particle abrasion and thus particle emission during use, i.e., sliding operation, very well compared to other plastic materials. Said materials are also particularly suitable for detachable plastic slide bars, e.g., the above described clip holders.

In another example the plastic slide bars may be made from or comprise an elastomer with viscoelasticity. Said elastomer may be a silicone rubber, a fluoroelastomer, polyether block amides, ethylene-vinyl acetate, polybutadiene, styrene/acrylates copolymers and such. Silicone rubbers were found to be particularly suitable. The elastomer may be a saturated rubber that cannot be cured by sulfur vulcanization in some embodiments or an unsaturated rubber that can be cured by sulfur vulcanization. The saturated rubber was found to be preferable for some embodiments. Said materials are particularly suitable for plastic slide bars comprising a tunnel and non-detachable plastic slide bars. An embodiment of a plastic slide bar comprising a tunnel may be a plastic slide hose. Thermoplastic elastomers were found to be particularly suitable. Each plastic slide bar having a tunnel may be flexible when the brackets are not inserted, e.g., a flexible silicone hose (they are essentially rigid, once the brackets are inserted).

Each plastic slide bar may have a length that is at least five times as large as the maximum width. In this case said plastic slide bars extend below a significant portion of the transfer plate. This distributes the force evenly, resulting in even less particle emission.

In some embodiments the plastic clip holder may have at least one rounded edge over and/or around which the transfer plate glides when the brackets lift the transfer plate away from the lower end. In some embodiments the clip elbow may have at least one rounded edge over and/or around which the transfer plate glides when the brackets lift the transfer plate away from the lower end.

In some embodiments two opposing central connection plates are pivotably connected to with their upper arms to two opposing lateral brackets and the opposing lower arms of the connection plates are mounted in opposing curved slits of an enclosure, wherein the brackets are also pivotably connected to said enclosure. It should be noted that also other connections are possible to achieve a lifting of a transfer plate. However, this lever system was found to be particularly efficient in terms of cost and reliability.

Each connection plates may in some embodiments be essentially T-shaped. The brackets may also be essentially U-shaped. It is to be understood that the shapes that are described as "essentially T-shaped" or "essentially U-shaped" relate to the general arrangement of arms. A T-shape implies that tow arms on one end are opposed by one arm on the other end. A Y-shaped arm is essentially also a T-shape as the angles are not decisive. A U-shaped arm has two arms pointing in one direction that are connected by a connecting section. Said connecting section may be curved, but a U-shaped arm may also have a flat connection section (comparable to a rectangle with one missing side). Each brackets may also be U-shaped in some embodiments.

Each connection plate may comprise a slidable plate pin that is mounted within the curved slit. Said slidable plate pin may be a screw that is detachably fastened to the connection plate, e.g., using a threaded mounting fixture of the connection plate. Additionally the connection plate may have a slit, in particular a straight slit, for the bracket pin of one of the brackets and a circular hole for a bracket pin of the other bracket. It may be that one bracket is connected by two pivotable and slidable bracket pins to the connection plate, whereas the other brocket is connected by two bracket pins that are only pivotable and not slidable.

Each connection plate may comprise a slit, in particular a straight slit, wherein a bracket pin is mounted.

The contact structure may be a flat metal framework of connected struts. In principle a plate is also possible on which the transfer plate is held. However, with struts it was found that less material is needed and the transfer plate is still mounted.

In some embodiments said struts may have a thickness that equals at least 20% of the width of the struts. In some of said embodiments said struts may have a thickness that equals at least 30% of the width of the struts. This results in a seemingly fragile framework of struts that was found to be very robust. The length of said struts usually may be several times larger than the thickness and width. In some embodiments the length is at least five times or even at least ten times larger than the width and/or the thickness of each strut.

Also the struts may form adjacent triangular structures. Triangular structures were found to be particularly robust. Said triangular structures may comprise triangular openings. For example the struts may formed a rectangle with diagonal struts connection the edges. Also in some embodiments the rectangle may have additional protruding triangular structures beyond said rectangle resulting in a wider contact area.

In some embodiments the wetting device comprises an enclosure with a first lateral side, a second lateral side and a bottom side, wherein the mechanical elevator is connected to the first and second lateral sides. Although it is possible to provide mechanical elevators without such enclosures, it was found that they are more robust with them. Mechanical elevators without such enclosures might be secured to the container itself.

The mechanical elevator may be detachably connected to the first and second lateral side by fastening means. Said fastening means may be bolts, screws, clamps, clip holders and other mechanical fastening means. Most suited were screws. It was found that decontamination with an autoclave is significantly improved if the mechanical elevator can be removed. In some embodiments the mechanical elevator itself can be disassembled for an even better decontamination. The mechanical elevator may have several monobloc pieces, such as the above described connection plates and brackets that are detachably connected by mechanical fastening means as described above.

In some embodiments the first and second lateral sides each may comprise a rectangular frame with an internal plate that has two arms connected to the upper side of the rectangular frame and one arm connected to the lower side of the rectangular frame, wherein the lower side of the rectangular frame is connected to the bottom side of the enclosure. In some embodiments said internal plate comprises a curved slot in which the above described connection plate is slidably mounted. Also the brackets may be pivotably connected to said internal plate, e.g., to the two arms connected to the upper side.

In some embodiments said enclosure may be a monobloc piece of metal. This results in a particularly robust design.

The enclosure may have been formed from a single plate by cutting and bending or punching and bending.

In some embodiments the lower end of the wetting device may be formed by the bottom side of the enclosure and the upper end of the wetting device may be formed by the top endings of the first lateral side and/or second lateral side. The bottom side may also comprise feet, wherein said feet are suited to stand on a container bottom.

In some embodiments the transfer plate may have a plate bottom and two opposing end sections with raised edges for retaining liquid and at least one opening for liquid between said end sections. Said two opposing end sections may in some embodiments be enclosed by raised edges in three directions. In some embodiments each raised edge may have three segments, i.e., two lateral segment and one end segment connecting the lateral segments. The at least one opening for liquid may be arranged between lateral segments of raised edges of opposing end sections. Said opening for liquid between said end sections may limit the raised edges and may partially be formed in the plate bottom and/or may have a length that is at least 25% of the total length of the plate. The transfer plate has the function of transferring a predefined amount of liquid. The amount of liquid is largely predefined by the geometry of the plate. If a lot of liquid shall be transferred, circumferential raised edges may be used, e.g., like with a bowl. If little liquid shall be transferred, opening for liquid may be implemented, e.g., like with a net that holds no liquid. Thus transfer plates with openings for little liquid are known and bowls for transfer of larger amounts liquid are also known. Surprisingly a combination of raised edges for retaining liquid with at least one opening for releasing liquid results in an improved transfer plate. It was found that said transfer plate can compensate some negative influences. Ideally the transfer plate is lifted absolutely horizontally, i.e., there is no incline at all. However, due to the applied force, vibrations or a slight inclination of the ground the wetting device is placed on, there may be a deviation from such a horizontal orientation. With the transfer plate as described above the amount of liquid is still largely predefined by the geometry of the plate even with some slight deviation from a horizontal orientation. Thus the described design is more reliable than other solutions. This may be at least partly because liquid needs more time to drain off from the plate and cannot drain off at the ends.

In some embodiments the mechanical elevator comprises at least one removable fluid displacer. The fluid displacer may be made of plastic or metal. The fluid displacer may be a single monobloc piece or have several parts. With a fluid displacer it was found that less fluid is needed. In some embodiments the fluid displacer displaces at least 50% of the liquid that would be in the container until the level at which the fluid displacer is fully covered, when the fluid displacer is made use of.

Said removable plastic fluid displacer may comprise recesses for receiving the brackets. This allows the brackets to lower further and results even less liquid to be needed.

The recesses may have an inclined wall for receiving the brackets when they are inserted into the recesses. Said incline may be between 20 and 80° compared to the orientation of the transfer plate, for example 30 to 50°. This construction of recesses displaces most liquid while allowing the brackets to be lowered further as described above. The brackets usually are not lowered vertically, but pivot into said recess.

The removable plastic fluid displacer may be made from a thermoplastic material. Suitable thermoplastic materials include polyacetals, polyethersulfones, polysulfones, polyether ketones, polyketones, polybutylene terephthalate or polytetrafluoroethylene. Rather suitable polymer materials include polyacetals such as polyoxymethylene.

Said removable plastic fluid displacer may be attached to the enclosure, e.g., the bottom side of said enclosure. In some suitable embodiments the plastic fluid displacer is made of two or more parts, each of which is attached to the enclosure. The recesses may be formed between said parts.

In some embodiments the bottom side of said enclosure has at least one opening for the fluid displacer. Said at least one opening (in case of several openings the openings) may constitute a large section of the total bottom side. The bottom side may be a frame for the fluid displacer. In some embodiments the at least one opening is essentially rectangular. The at least one opening has two potential advantages. It may provide more space for the fluid displacer and thus less water is needed (in the area of the opening fluid is displaced in this case). Also said at least one opening may help in securing the fluid displacer, e.g., as a plug-in system wherein the fluid displacer clicks into the at least opening.

In some embodiments the bottom side has a number of openings for an equal number of parts of a multipart fluid displacer. Each part of the fluid displacer may fit into the an corresponding opening.

The removable plastic fluid displacer may be autoclavable.

In some embodiments the wetting device is apart from the plastic slide bars and/or plastic fluid displacer made from metal, i.e., the wetting device is made completely from metal with the exception of the plastic slide bars and/or the plastic fluid displacer (if there is a plastic fluid displacer implemented).

The present disclosure also relates to a wetting device with an upper end and a lower end, comprising a transfer plate for liquid as well as a mechanical elevator, wherein the mechanical elevator contains a contact structure and lifts the transfer plate away from the lower end, if the contact structure is pressed towards the lower end, wherein the transfer plate has two opposing end sections with raised edges and at least one opening for liquid between said end sections. The advantages of such a transfer plate have already been discussed.

The present disclosure also relates to a wetting device with an upper end and a lower end, comprising a transfer plate for liquid as well as a mechanical elevator, wherein the mechanical elevator contains a contact structure and lifts the transfer plate away from the lower end, if the contact structure is pressed towards the lower end, wherein the mechanical elevator comprises at least one removable plastic fluid displacer. The advantages of such a fluid displacer have already been discussed.

The present disclosure also relates to a cleaning trolley comprising the wetting device as described above.

Figure 2:
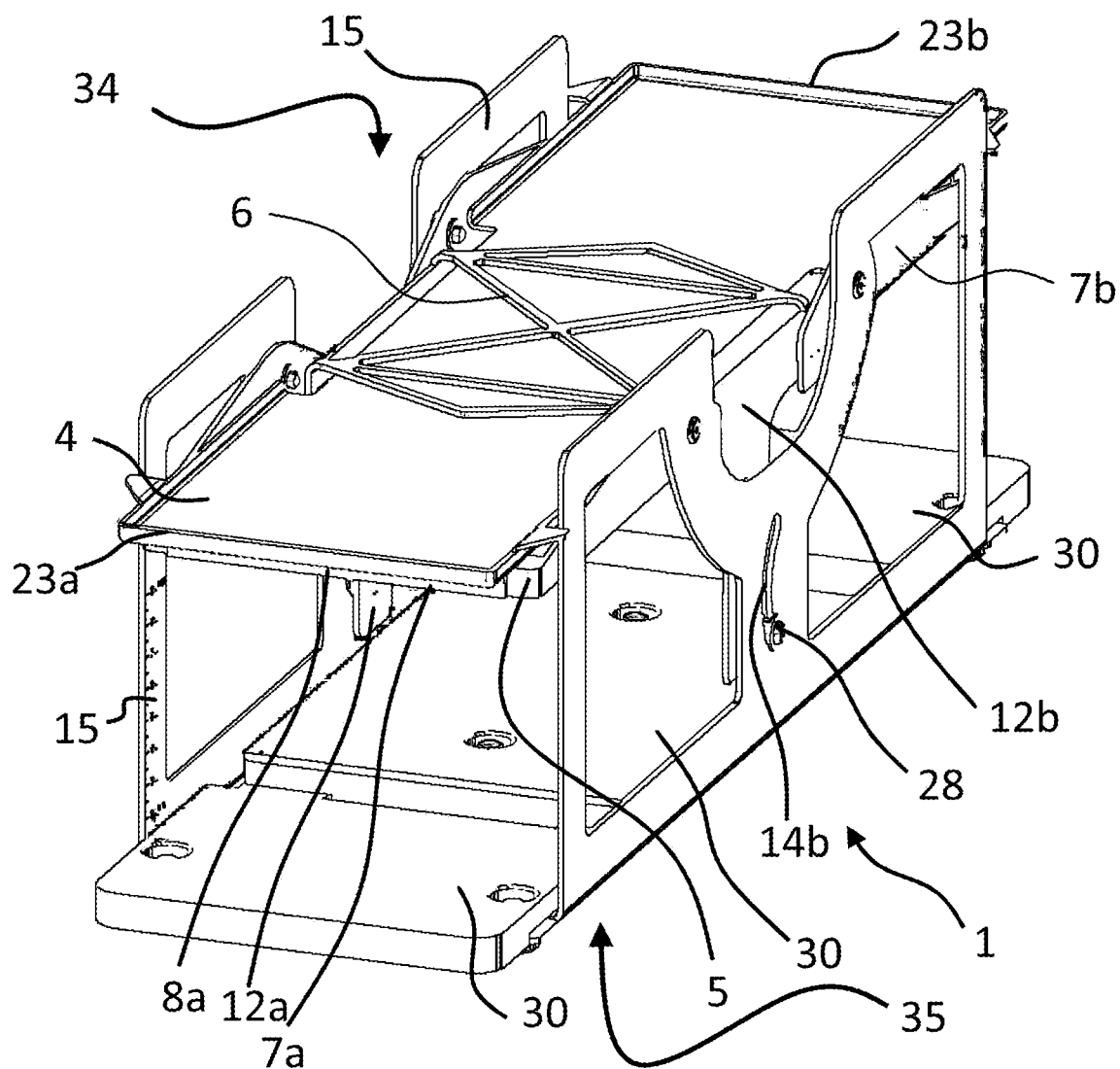
FIG. 2 shows a perspective view of an embodiment of wetting device with the transfer plate in a lifted position.

FIG. 1 shows an embodiment of a wetting device 1 for flat mops with an upper end 34 and a lower end 35. The wetting device 1 of FIG. 1 with an upper end 34 and a lower end 35 has a transfer plate 4 for liquid as well as a mechanical elevator 5, wherein the mechanical elevator 5 contains a contact structure 6 and brackets 7a, 7b. The brackets 7a, 7b of FIG. 1 are in a lowered position and may be lifted into a lifted position as shown in FIG. 2, when the contact structure 6 is pressed downwards. FIG. 1 depicts connection plates 12a, 12b. The connection plates 12a, 12b each may have upper arms 13a, 13b and lower arms 13c that are mounted in opposing curved slits 14a, 14b with movable plate pins 28. The mechanical elevator 5 may comprise at least one removable plastic fluid displacer 30. Said connection plates 12a, 12b may be connected to an enclosure 15 with an internal plate 20a, 20b comprising said curved slits 14a, 14b.

FIG. 2 shows again the embodiment of FIG. 1. FIG. 2 differs in that the brackets 7a, 7b of FIG. 1 are in a raised position and consequently also the transfer plate 4 is lifted. The mechanical elevator 5 of the wetting device 1 with an upper end 34 and a lower end 35 may lift the transfer plate 4 with its raised edges 23a, 23b into the position of FIG. 2. The contact structure 6 has been pressed downwards do achieve this configuration. It is thus lower than in FIG. 1. This configuration usually is only maintained as long as a force is applied to the contact structure 6. If the force is removed from contact structure 6 gravitation would move the mechanism into the configuration of FIG. 1. FIG. 2 also shows the connection plates 12a, 12b which have been lowered. The slidable plate pin 28 in the slit 14b is moved downwards together with the connection plates 12a, 12b that may be attached to the contact structure 6. The two opposing connection plates 12a, 12b may be pivotably connected with their upper arms to two opposing lateral brackets 7a, 7b and the opposing lower arms 13a, 13b of the connection plates may be mounted in opposing curved slits 14a, 14b of an enclosure 15, wherein the brackets may be also pivotably connected to said enclosure 15. In FIG. 2 also one the plastic slide bars 8a and a fluid displacer 30 is depicted and will be discussed in detail in connection with FIGS. 3 and 5.

Figure 3:
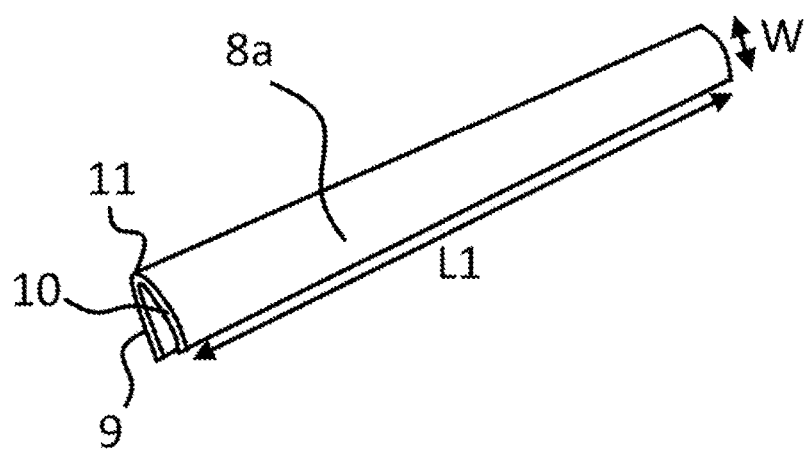
FIG. 3 shows a perspective view of a detached plastic slide bar.

FIG. 3 shows an embodiment of a plastic slide bar 8a. The plastic slide bar 8a may be a detachable clip holder, having two clamping thighs 9, 10 that clamp the corresponding bracket (not shown in FIG. 3). The plastic slide bar 8a may have a length L1 that is at least five times as large as the maximum width W. The plastic slide bar 8a may have at least one rounded edge 11 over which the transfer plate 4 glides when the brackets 7a, 7b lift the transfer plate 4 away from the lower end 35. The second plastic slide bar 8b may be built as a mirror image or identically (not shown in FIG. 3).

Figure 4:
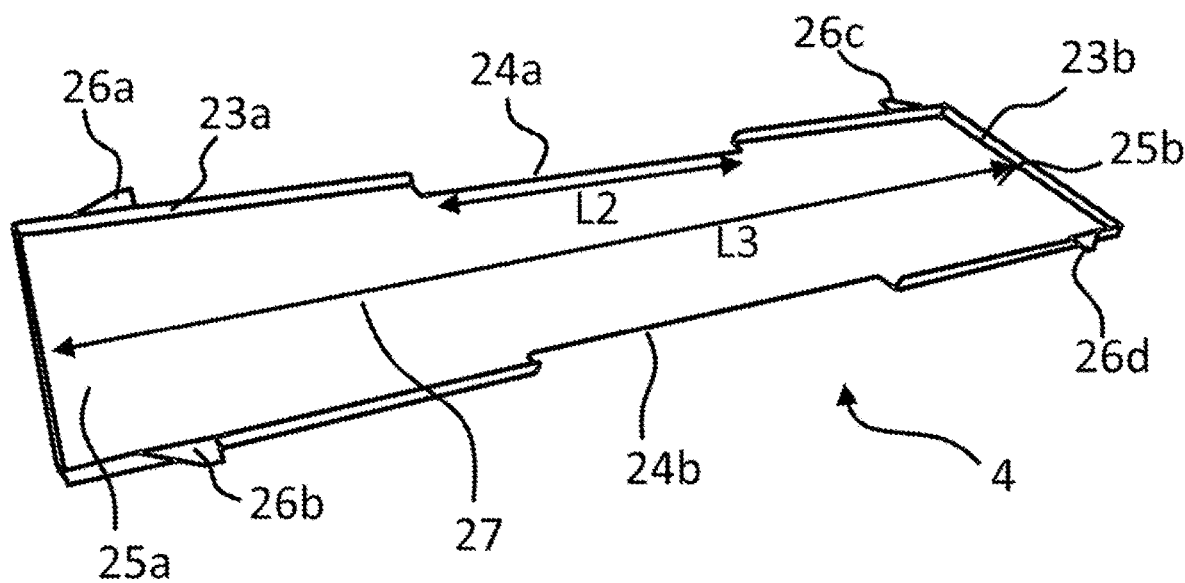
FIG. 4 shows a perspective view of an embodiment of the transfer plate.

FIG. 4 shows an embodiment of a transfer plate 4. Said transfer plate 4 may have a plate bottom 27 and two opposing end sections 25a, 25b with raised edges 23a, 23b and at least one opening 24a, 24b for liquid between said end sections 25a, 25b. Said two opposing end sections 25a, 25b may be enclosed by said raised edges 23a, 23b in three directions. The at least one opening 24a, 24b for liquid between said end sections 25a, 25b may limit the raised edges 23a, 23b and may be partially formed in the plate bottom 27 and/or may have a length L2 that is at least 25% of the total length of the plate L3. Stoppers 26a, 26b, 26c, 26d can be implemented to ensure that the transfer plate 4 is secured.

Figure 5:
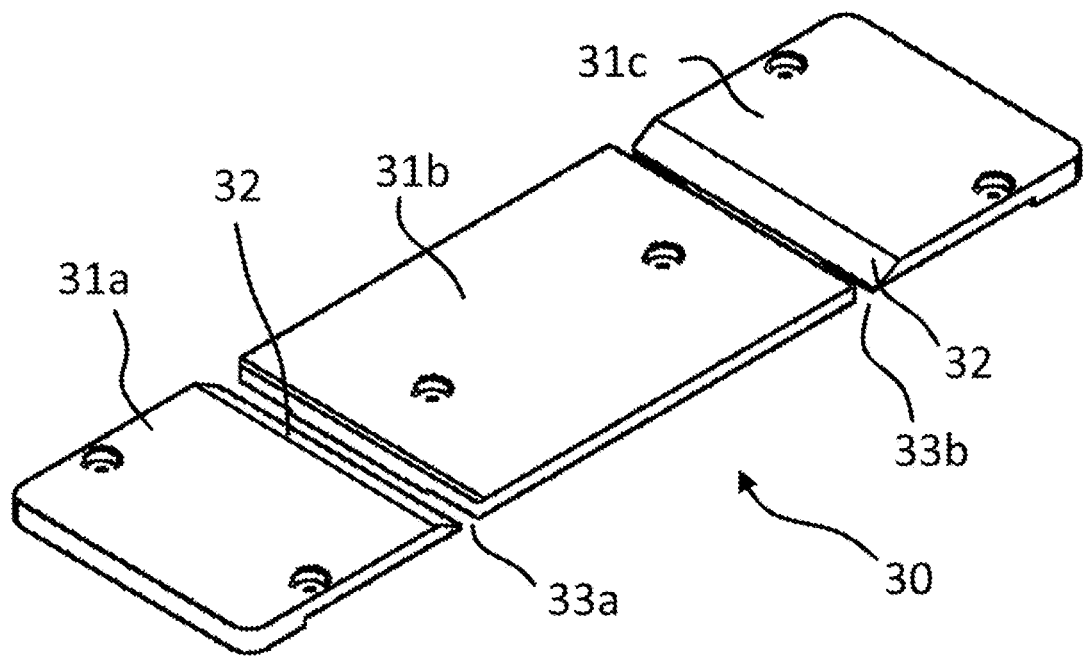
FIG. 5 shows a perspective view of an embodiment of the fluid displacer.

FIG. 5 shows an embodiment of a removable plastic fluid displacer. Said removable plastic fluid displacer may comprise recesses 33a, 33b for receiving the brackets not shown in FIG. 4. Said recesses 33a, 33b may have inclined walls 32 for receiving the brackets when they are inserted into the recesses. The fluid displacer may have several parts 31a, 31b, 31c, wherein the recesses 33a, 33b are also defined by the distances between said parts.

Figure 6:
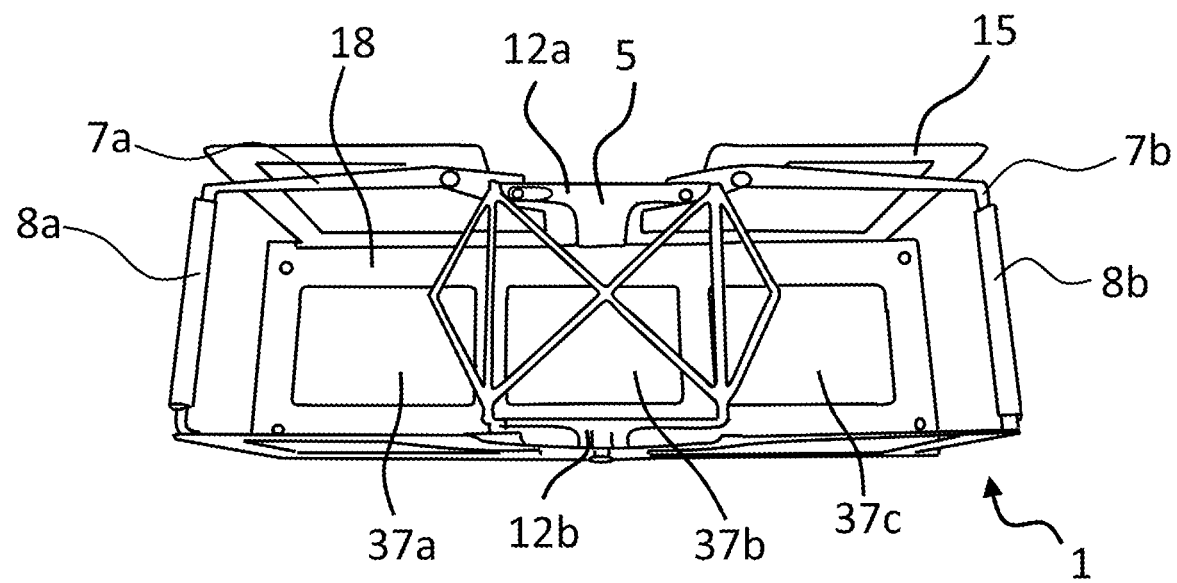
FIG. 6 shows a top down perspective view of an embodiment of wetting device with the transfer plate in a lifted position.

FIG. 6 shows a top down view of an embodiment of a wetting device 1 with the brackets 7a, 7b in a raised position. The transfer plate 4 has been detached to show the mechanism better. The brackets 7a, 7b have a U-shape and each bracket 7a, 7b is connected to at least one plastic slide bar 8a, 8b. The opposing brackets 7a, 7b are connected by connection plates 12a, 12b of the mechanical elevator 5. Said brackets are also pivotably connected to the enclosure 15. In this embodiments the bottom side 18 of said enclosure has at openings 37a, 37b, 37c for the fluid displacer. The fluid displacer is not shown to enable a view upon said openings.

Figure 7:
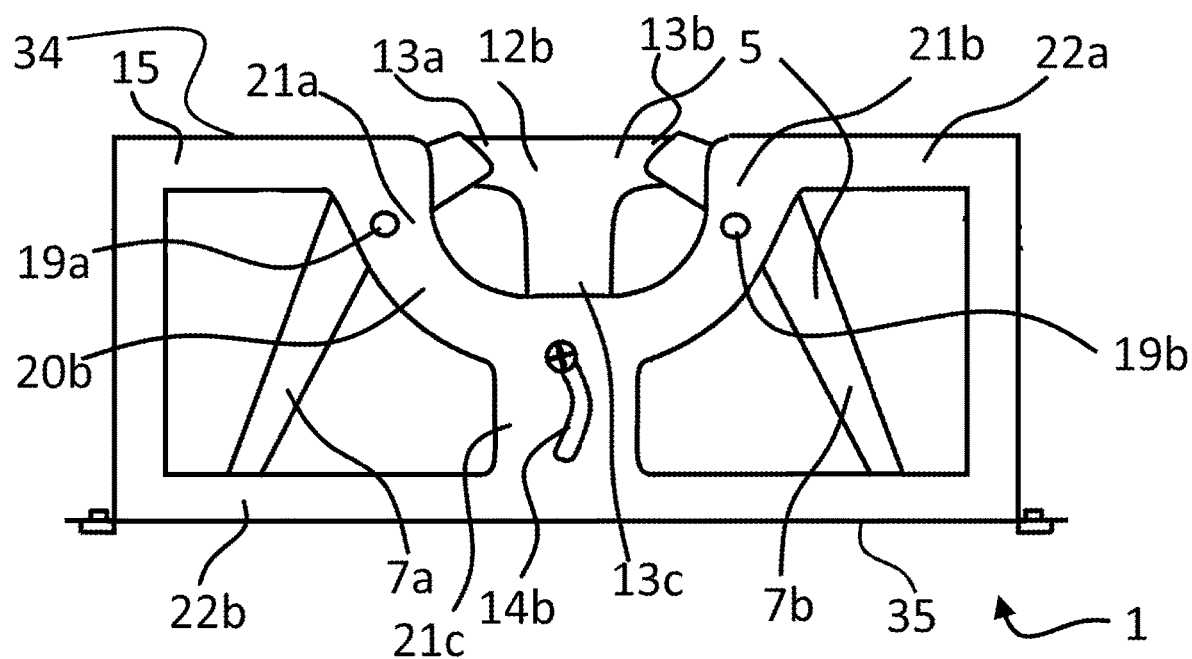
FIG. 7 shows a schematic side on view of an embodiment of wetting device with the transfer plate in a lowered position.

FIG. 7 shows a schematic side on view of an embodiment of the wetting device 1 with an upper end 34 and a lower end 35 with the mechanical elevator 5 in a lowered configuration. In FIG. 7 a central connection plates 12b is pivotably connected with its upper arms 13a, 13b to two opposing lateral brackets 7a, 7b and the opposing lower arm 13c of the connection plate is mounted in a curved slit 14b of the enclosure 15, wherein the brackets are also pivotably connected at pivot points 19a, 19b to said enclosure 15. The enclosure 15 comprises a rectangular frame with an internal plate 20b that has two arms 21a, 21b connected to the upper side 22a of the rectangular frame and one arm 21c connected to the lower side 22b of the rectangular frame, wherein the lower side 22a of the rectangular frame is connected to the bottom side of the enclosure 15. The slit 14b for mounting the T-shaped plate 12b is part of the arm 21c.

Figure 8:
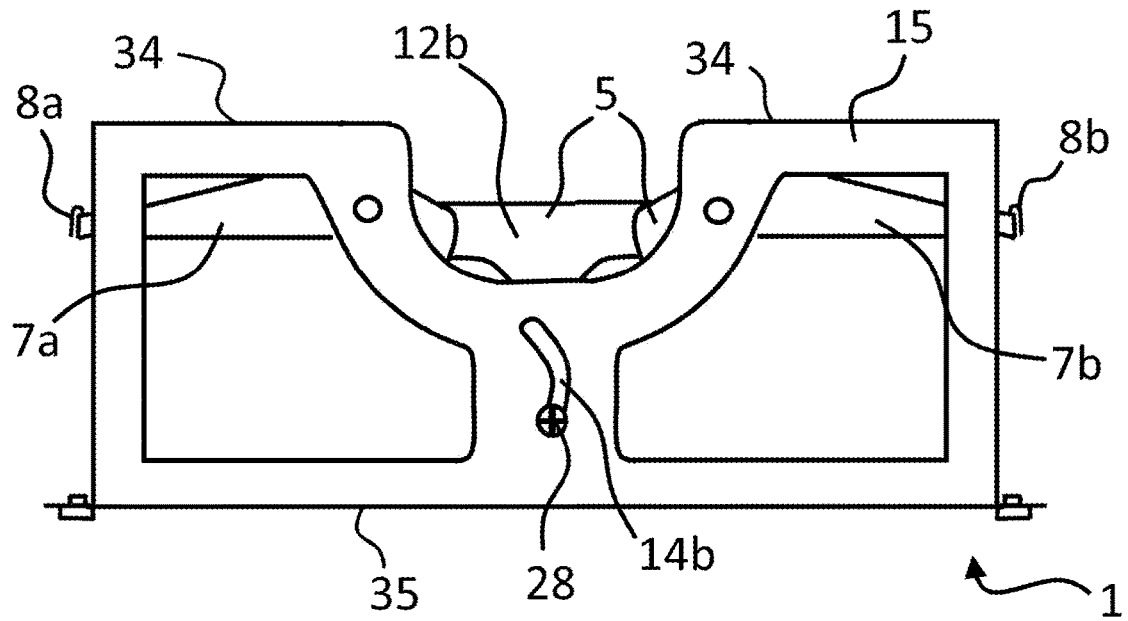
FIG. 8 shows a schematic side on view of an embodiment of wetting device with the transfer plate in a lifted position.

FIG. 8 shows a schematic side on view of an embodiment of the wetting device 1 with an upper end 34 and a lower end 35 with the mechanical elevator 5 in a raised configuration. It is the same embodiment as FIG. 7, but a different configuration. The brackets 7a, 7b are raised and contain plastic slide bars 8a, 8b. In contrast to FIG. 7 the slidable plate pin 28 holding the connection plate 12b moved downwards together with said connection plate 12b. The slidable plate pin 28 is secured in the curved slit 14b of the enclosure 15.

Figure 9:
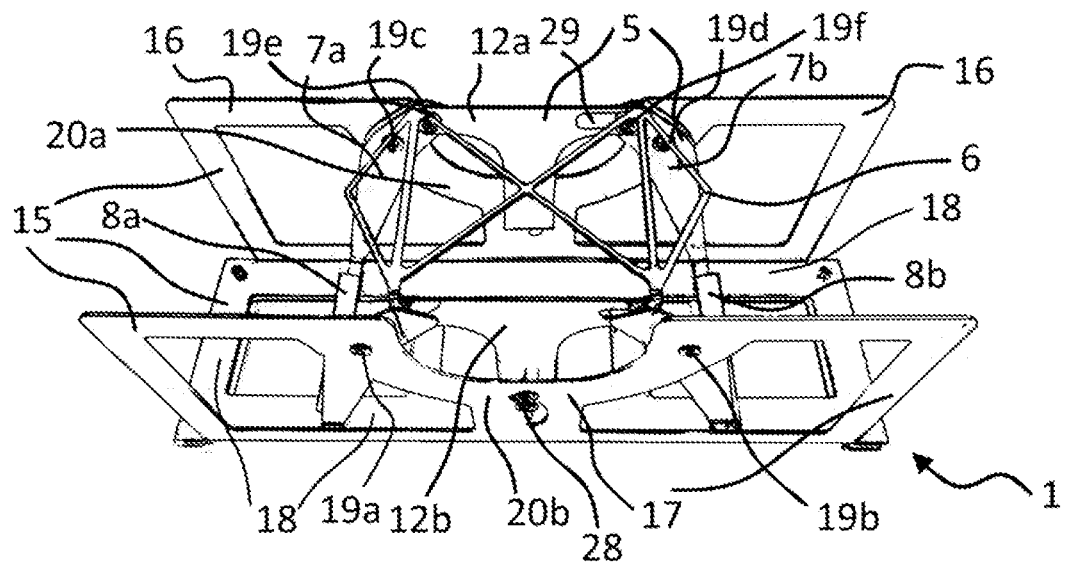
FIG. 9 shows a perspective view of an embodiment of wetting device without the transfer plate with the brackets in a lowered position.

FIG. 9 shows a perspective view of an embodiment of wetting device 1 without a transfer plate with the brackets 7a, 7b in a lowered position. Said brackets contain plastic slide bars 8a, 8b. The mechanical elevator 5 contains a contact structure 6 and brackets 7a, 7b. Said brackets 7a, 7b are pivotable about fastening means 19a, 19b, 19c, 19d, which also connect the first and second lateral side 16, 17 of the enclosure 15. Said enclosure 15 with said first lateral side 16 and said second lateral side 17 also has a bottom side 18, wherein the mechanical elevator 5 is connected to the first and second lateral side 16, 17. This embodiment contains no removable plastic fluid displacer. Connection plates 12a, 12b are connected to internal plates 20a, 20b of the enclosure 15 by slidable plate pins 28 within curved slits of the enclosure (cf., FIGS. 1, 2, 6, 7). The brackets 7a, 7b are pivotably connected to the connection plates 12a, 12b by connecting bracket pins 19e and 19f. On the opposite side similar connecting bracket pins 19g and 19h are not visible from this perspective (cf., FIG. 12).

Figure 10:
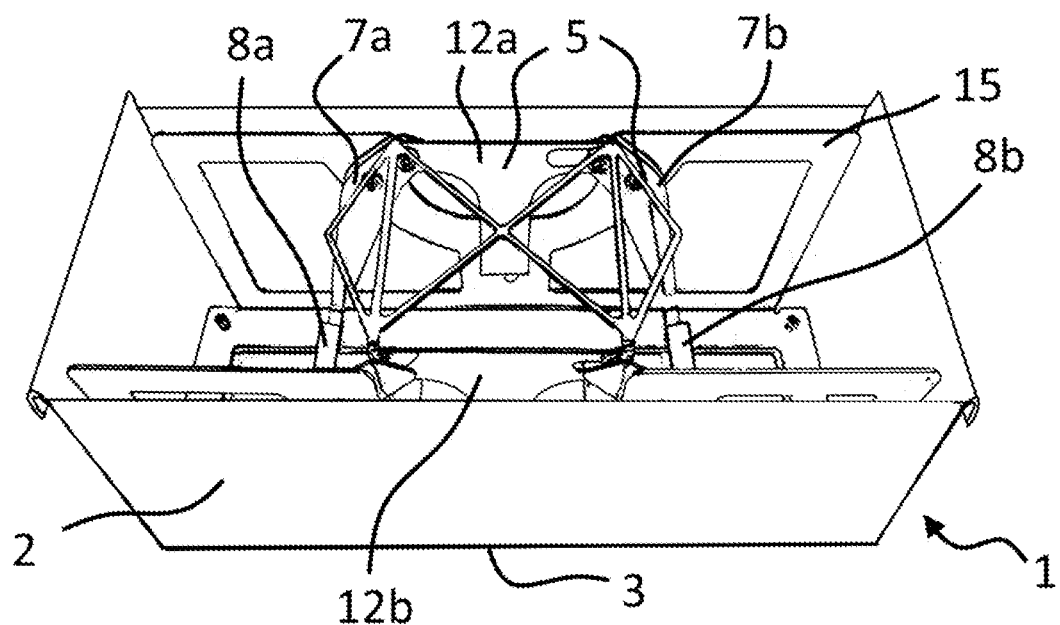
FIG. 10 shows a perspective view of an embodiment of wetting device within a container and without transfer plate with the brackets in a lowered position.

FIG. 10 shows a perspective view of the embodiment of FIG. 9 within a container 2 with the brackets in a lowered position. The mechanical elevator 5 and the enclosure 15 within the container 2 have already been discussed in connection with FIG. 9. The container 2 has a container bottom 3.

Figure 11:
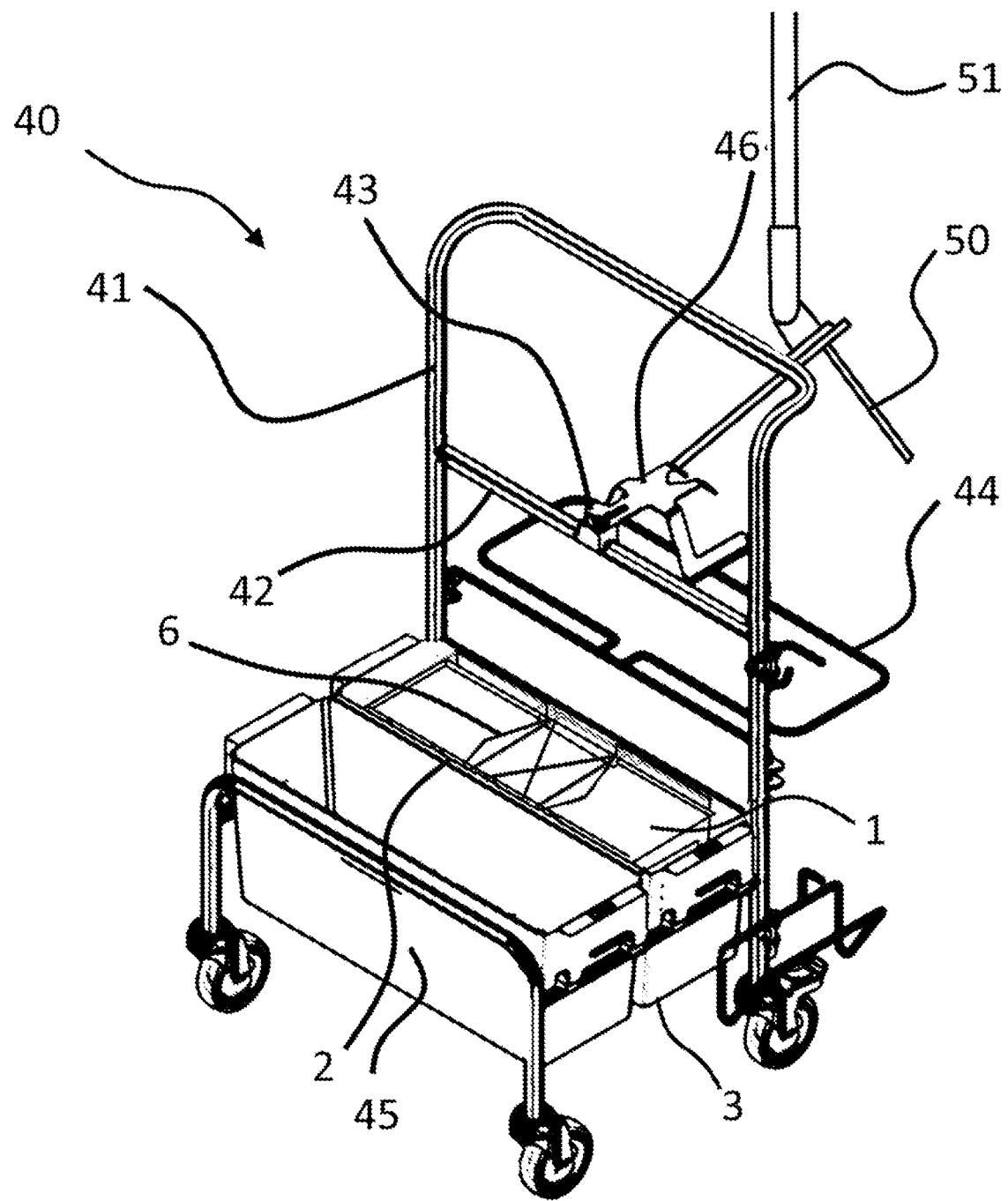
FIG. 11 shows a cleaning trolley with an embodiment of a wetting device.

FIG. 11 shows an embodiment of a cleaning trolley 40 with an embodiment of a wetting device 1. The wetting device 1 comprises a contact structure 6 with a container 2 with a container bottom 3. Other details of the wetting device 1 can be derived from previous figures. Said wetting device 1 is part of the cleaning trolley. Said cleaning trolley 40 also has another container 45 for clean textile covers for flat mops. The cleaning trolley 40 has a handle 41 with a traverse bar 42, to which a discharge system 46 for flat mop covers is attached by a fastening means 43, e.g., a screw. Below said discharge system 46 is a frame 44 for holding bags. An embodiment of flat mop 51 with a flat mop head 50 and without a textile cover is depicted as well.

Figure 12:
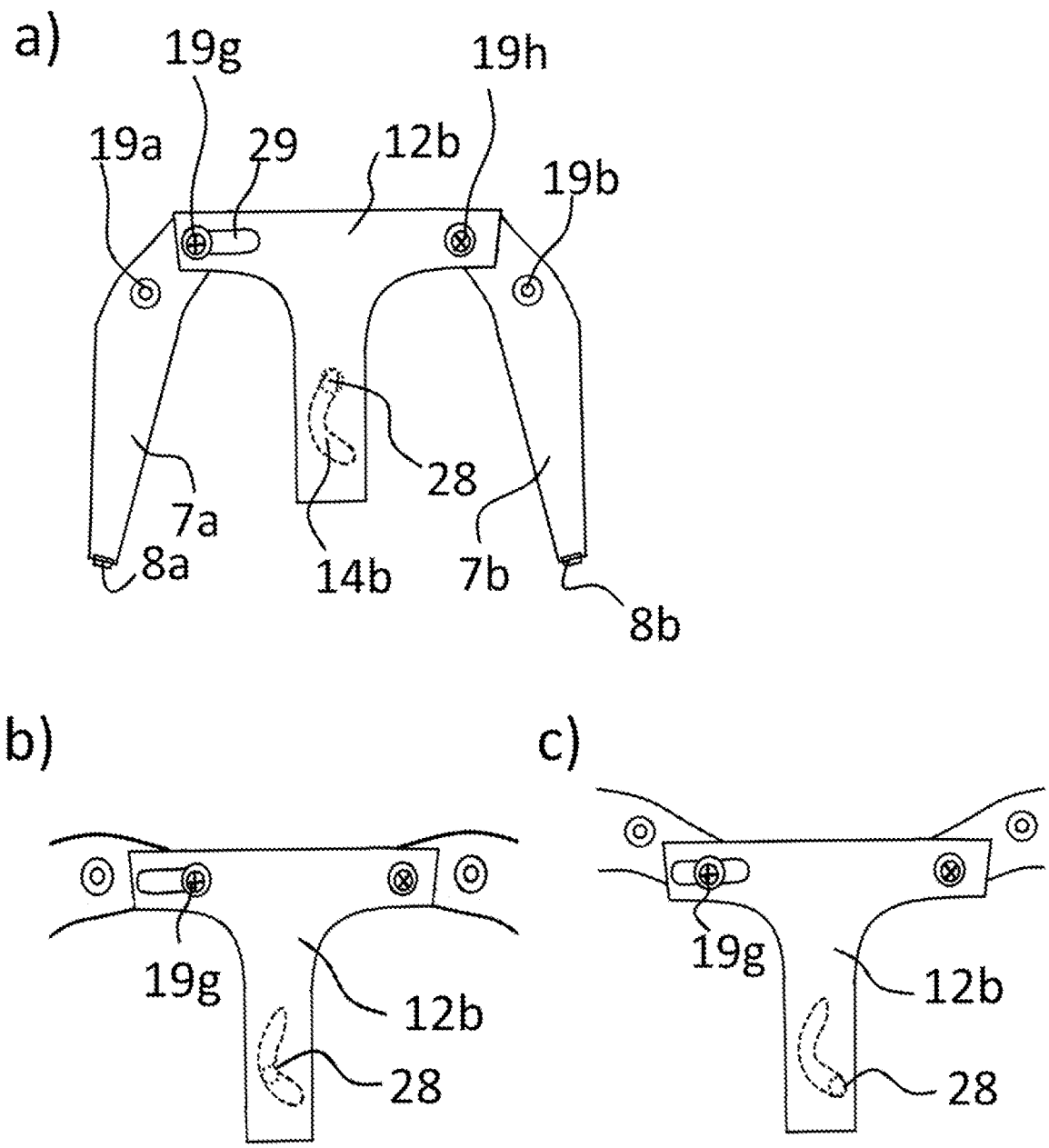
FIG. 12 shows a schematic representation for a lifting mechanism of the brackets.

FIG. 12 shows in a) a schematic display of the brackets 7a, 7b with plastic slide bars 8a, 8b in a lowered position. Said brackets 7a, 7b may be pivotably fixed to the enclosure 5 by fastening means 19a, 19b. The connection plate 12b may be mounted in a curved slit 14b of the enclosure the position of the slit 14b is indicated, wherein the slidable plate pin 28 is in a high position. The brackets 7a, 7b may be pivotably connected to the connection plate 12b by two connecting bracket pins 19g and 19h and one of said connecting bracket pins 19g is mounted slidable in a straight slit 19g of the connection plate 12b. On the other side no such slit is necessary for connecting bracket pin 19h in this embodiment of a mechanism. The slit 14b may be curved in such a way that it follows the pivotal movement of the bracket 7b, but not the opposing bracket 7a. A curved slit 29 compensates the pivotal movement of bracket 7a. In b) an intermediate position is shown, wherein the brackets 7a, 7b are lifted to some degree, but not fully. In c) the final position is shown, in which the brackets 7a, 7b are lifted completely. The slidable plate pin 28 in slit 14b also serves as a stopper for this movement.

Figure 13:
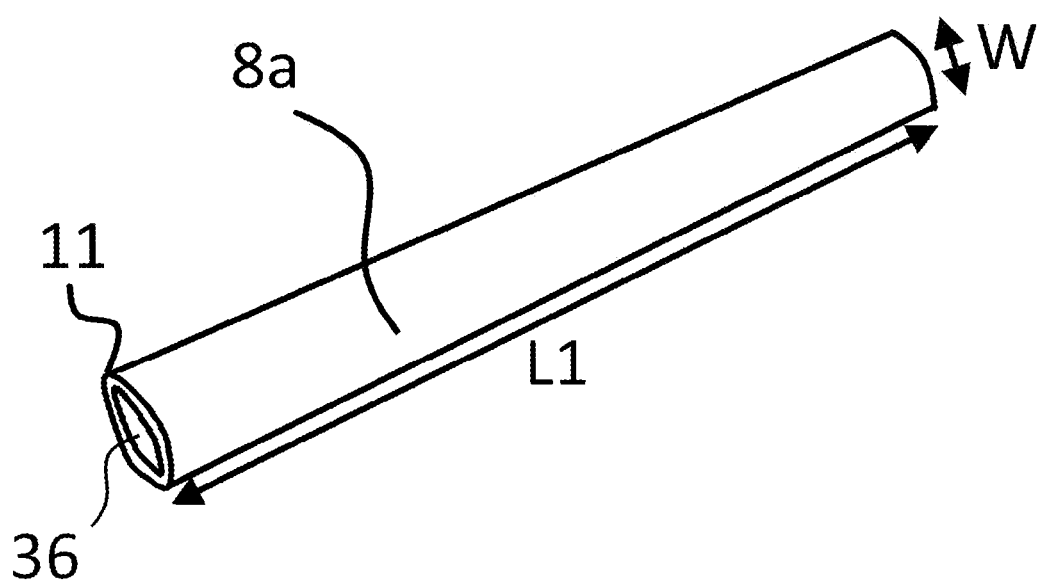
FIG. 13 shows a perspective view of another embodiment of a plastic slide bar.

FIG. 13 shows another embodiment of plastic slide bar 8a. This plastic slide bar may be made of an elastomer. The plastic slide bar may comprise a tunnel 36 that surrounds the corresponding bracket (not shown in FIG. 13). The plastic slide bar may have a length L1 that is at least five times as large as the maximum width W. The plastic slide bar may have at least one rounded edge 11 over which the transfer plate 4 glides when the brackets 7a, 7b lift the transfer plate 4 away from the lower end 35. The second plastic slide bar 8b may be built as a mirror image or identically (not shown in FIG. 13).

The features of the invention disclosed in the above description, the claims and the drawings can be essential, both individually and in any combination, to implement the invention in its various embodiments.

The invention claimed is:

1. A wetting device for flat mops, comprising:
   an upper end, a lower end, a transfer plate for liquid, and a mechanical elevator,
   wherein the mechanical elevator contains a contact structure, brackets, and plastic slide bars,
   wherein each bracket is connected to at least one plastic slide bar and the brackets lift the transfer plate away from the lower end if the contact structure is pressed towards the lower end,
   wherein the plastic slide bars move apart from each other when the transfer plate lifts away from the lower end and wherein the transfer plate lies upon said plastic slide bars during said movement of the plastic slide bars apart from each other,
   wherein each plastic slide bar has a length that is at least five times larger than its maximum width and wherein each plastic slide bar is detachable from its corresponding bracket,
   wherein the contact structure is a flat metal framework of connected struts, and
   wherein the plastic slide bars are clip holders, each having two clamping thighs that clamp the corresponding bracket.

2. The wetting device according to claim 1, wherein the plastic slide bars comprise or are made from polyacetals, polyethersulfones, polysulfones, polyether ketones, polyketones, polybutylene terephthalate, or polytetrafluoroethylene.

3. The wetting device according to claim 1, wherein each plastic slide bar has at least one rounded edge over which the transfer plate glides when the brackets lift the transfer plate away from the lower end.

4. The wetting device according to claim 1, further comprising two opposing central connection plates having upper arms and opposing lower arms, wherein the two opposing central connection plates are pivotably connected with their upper arms to the brackets, wherein the brackets are two opposing lateral brackets, and the opposing lower arms of the two opposing central connection plates are mounted in opposing curved slits of an enclosure, wherein the brackets are also pivotably connected to said enclosure.

5. The wetting device according to claim 1, wherein the struts have a thickness that equals at least 20% of a width of the struts.

6. The wetting device according to claim 1, wherein the struts form adjacent triangular structures.

7. The wetting device according to claim 1, wherein the wetting device comprises an enclosure with a first lateral side, a second lateral side, and a bottom side, wherein the mechanical elevator is connected to the first and second lateral sides.

8. The wetting device according to claim 7, wherein the mechanical elevator is detachably connected to the first and second lateral sides by fastening means.

9. The wetting device according to claim 7, wherein the first and second lateral sides each comprises a rectangular frame with an internal plate that has two arms connected to an upper side of the rectangular frame and one arm connected to a lower side of the rectangular frame, wherein the lower side of the rectangular frame is connected to the bottom side of the enclosure.

10. The wetting device according to claim 7, wherein the enclosure is a monobloc piece of metal.

11. The wetting device according to claim 1, wherein the transfer plate has a plate bottom and two opposing end sections with raised edges and at least one opening for liquid between said end sections.

12. The wetting device according to claim 11, wherein the two opposing end sections are each enclosed by two lateral segments and one end segment connecting the two lateral segments.

13. The wetting device according to claim 12, wherein the at least one opening for liquid between said end sections limits the lateral segments and end segment and is partially formed in the plate bottom and/or has a length that is at least 25% of the total length of the transfer plate.

14. The wetting device according to claim 1, wherein the mechanical elevator comprises at least one removable plastic fluid displacer.

15. The wetting device according to claim 14, wherein the at least one removable plastic fluid displacer comprises recesses for receiving the brackets.

16. The wetting device according to claim 1, wherein the wetting device is, apart from the plastic slide bars and/or plastic fluid displacer, made from metal.

17. The wetting device according to claim 1, wherein said wetting device is a cleanroom wetting device.

18. A cleaning trolley comprising the wetting device of claim 1.

19. The cleaning trolley according to claim 18, wherein said cleaning trolley is a cleanroom cleaning trolley.

* * * * *